(12) United States Patent
Taguchi et al.

(10) Patent No.: US 7,850,909 B2
(45) Date of Patent: Dec. 14, 2010

(54) ANALYTICAL TOOL

(75) Inventors: Takayuki Taguchi, Kyoto (JP); Shigeru Kitamura, Kyoto (JP); Yuichiro Noda, Kyoto (JP)

(73) Assignee: ARKRAY, Inc., Kyoto (JP)

( * ) Notice: Subject to any disclaimer, the term of this patent is extended or adjusted under 35 U.S.C. 154(b) by 1111 days.

(21) Appl. No.: 10/529,120

(22) PCT Filed: Sep. 25, 2003

(86) PCT No.: PCT/JP03/12295

§ 371 (c)(1),
(2), (4) Date: Mar. 25, 2005

(87) PCT Pub. No.: WO2004/029619

PCT Pub. Date: Apr. 8, 2004

(65) Prior Publication Data

US 2006/0045799 A1    Mar. 2, 2006

(30) Foreign Application Priority Data

Sep. 26, 2002  (JP) .............................. 2002-281101

(51) Int. Cl.
 *G01N 33/00* (2006.01)
(52) U.S. Cl. .......................... 422/57; 422/50; 422/68.1; 422/73; 422/99
(58) Field of Classification Search .................. 422/50, 422/68.1, 73, 99, 57
See application file for complete search history.

(56) References Cited

U.S. PATENT DOCUMENTS

| | | | |
|---|---|---|---|
| 4,753,776 A | 6/1988 | Hillman et al. | |
| 4,868,129 A | 9/1989 | Gibbons et al. | |
| 5,460,974 A | 10/1995 | Kozak et al. | |
| 6,315,738 B1 | 11/2001 | Nishikawa et al. | |
| 6,383,452 B1 | 5/2002 | Miyake et al. | |
| 6,615,856 B2 * | 9/2003 | McNeely et al. | 137/14 |
| 6,632,399 B1 * | 10/2003 | Kellogg et al. | 422/72 |
| 2001/0028862 A1 | 10/2001 | Iwata et al. | |
| 2004/0121356 A1 | 6/2004 | Yamagata et al. | |
| 2006/0008381 A1 | 1/2006 | Taguchi et al. | |

FOREIGN PATENT DOCUMENTS

| | | |
|---|---|---|
| EP | 0 698 413 | 8/1995 |
| EP | 0 806 666 | 2/1997 |
| EP | 1 329 717 | 10/2001 |
| JP | 63-177059 | 7/1988 |
| JP | 1-257268 | 10/1989 |
| JP | 3-59457 | 3/1991 |
| JP | 6-201704 | 7/1994 |

(Continued)

*Primary Examiner*—Sam Siefke
(74) *Attorney, Agent, or Firm*—Hamre, Schumann, Mueller & Larson, P.C.

(57) ABSTRACT

An analyzing tool (Y) has a liquid-introducing opening (61), one or more flow passages (51) through which a sample liquid introduced from the liquid-introducing opening (61) is moved, and a separation film (8) for filtrating the sample liquid supplied to the liquid-introducing opening (61) and then introducing the liquid filtrated to the one or more flow passages (51). The analyzing tool (Y) is structured such that a liquid sample is filtrated by being advanced in the thickness direction of the separation film (8). The flow passage (51) is structured such that the sample liquid is moved by, for example, a capillary phenomenon.

20 Claims, 12 Drawing Sheets

FOREIGN PATENT DOCUMENTS

| | | |
|---|---|---|
| JP | 8-105901 | 4/1996 |
| JP | 8-114539 | 5/1996 |
| JP | 10-2875 | 1/1998 |
| JP | 10-10125 | 1/1998 |
| JP | 10-501340 | 2/1998 |
| JP | 10-197526 | 7/1998 |
| JP | 10-206417 | 8/1998 |
| JP | 10-513259 | 12/1998 |
| JP | 2000-199761 | 7/2000 |
| JP | 2000-266759 | 9/2000 |
| JP | 2001-50952 | 2/2001 |
| JP | 2002-71684 | 3/2002 |
| JP | 2002-202310 | 7/2002 |
| JP | 2002-243726 | 8/2002 |
| JP | 2002-243734 | 8/2002 |
| WO | WO 95/33986 | 12/1995 |
| WO | WO 96/23223 | 8/1996 |
| WO | WO 98/08606 | 3/1998 |

\* cited by examiner

ANALYTICAL TOOL

TECHNICAL FIELD

The present invention relates to an analytical tool used for analyzing a particular component contained in a sample liquid (such as blood or urine, for example).

BACKGROUND ART

In an analysis method, reaction liquid obtained upon reaction of a sample and a reagent is analyzed by an optical technique, for example. In such a method for analyzing a sample, use is made of an analytical tool for providing a reaction field. For example, there exist analytical tools which are designed to remove solid components in the sample liquid before the sample liquid is supplied to reagent portions. Examples of such analytical tools include one shown in FIGS. 13 and 14 and one shown in FIGS. 15 and 16 of the present application (See JP-A 2002-508698A and JP-A 8-114539, for example).

The analytical tool 9A shown in FIGS. 13 and 14 includes a substrate 90, a cover 91, and a filter 92 interposed therebetween. The substrate 90 is formed with a space 90a in which the filter 92 is fitted. The cover 91 is formed with a liquid introduction port 92a located above the filter 92. The filter space 90a is connected to a discharge region 90b. In the analytical tool 9A, liquid is introduced through the liquid introduction port 92a to the filter 92 for removal of solid components and then guided to the discharge region 90b.

The analytical tool 9B shown in FIGS. 15 and 16 includes a sample receiving port 93, a first sample treatment chamber 94 for removing a substance causing measurement error, a first measurement chamber 95 for measuring a pre-reaction value, a second sample treatment chamber 96 including a reagent portion for reaction with a target substance, a second measurement chamber 97 for measuring optical characteristics of a reaction product of the target substance and the reagent, a filter 98 provided in the first sample treatment chamber 94 and directly below the sample receiving port 93, and a pump connection port 99. In the analytical tool 9B, a sample liquid is introduced through the sample liquid receiving port 93 to the filter 98 for removal of solid components and then guided to the first sample treatment chamber 94. With a pump connected to the pump connection port 99 of the analytical tool 9B, the sample liquid is sucked by the motive power of the pump for movement through the chambers 94-97.

In the analytical tools 9A and 9B, the removal of solid components at the filters 92, 98 is performed mainly when the sample liquid moves in the plane direction of the filters 92, 98. Therefore, in the analytical tools 9A and 9B, a large filtration length can be attained, so that efficient removal of solid components is expected. On the other hand, however, there is a fear that the removal of solid components takes long time and the measurement time becomes long due to the large filtration length and a long retention time of the sample liquid in the filters 92, 98. Such a fear is serious in an analytical tool designed to move a sample liquid by utilizing capillary action. Moreover, in such an analytical tool as a microdevice which has a flow path of a small sectional area, the movement of a sample liquid through the small flow path by capillary action becomes difficult when the sample liquid has a high viscosity. In such a case again, the above fear is serious.

When a sample liquid is moved by utilizing motive power of a pump as is in the analytical tool 9B, the sample liquid can be moved relatively easily, so that the above fear relating to the measurement time is not serious. However, since the apparatus for performing analysis by using the analytical tool 9B need be provided with a pump, the cost for the apparatus increases correspondingly. Moreover, the use of the pump increases the cost required for a single time of measurement.

DISCLOSURE OF THE INVENTION

An object of the present invention is to provide an analytical tool which is capable of removing solid components contained in a sample liquid without increasing the measurement time and which is advantageous in terms of cost.

According to the present invention, there is provided an analytical tool comprising a liquid introduction port, one or a plurality of flow paths for moving a sample liquid introduced through the liquid introduction port, and a separation film for filtering the sample liquid supplied to the liquid introduction port and then introducing the sample liquid to the one or a plurality of flow paths. The sample liquid is caused to move through the separation film in the thickness direction of the separation film for filtration.

In the analytical tool, the sample liquid is moved in the thickness direction of the separation film for removal of solid components contained in the sample liquid. Therefore, as compared with the structure in which the sample liquid is moved in the plane direction of the separation film, the retention time of the sample liquid in the separation film becomes shorter. As a result, the sample liquid does not receive so high resistance in the separation film and can pass through the separation film in a relatively short period of time. Thus, the time necessary for the removal of solid components and the measurement time can be shortened. Since the resistance in the movement of the sample liquid is low, the sample liquid can be moved by capillary action. Therefore, the sample liquid need not be moved by utilizing the motive power of a pump, so that the apparatus for performing measurement by using the analytical tool can be manufactured at a relatively low cost. Moreover, since the motive power of a pump need not be utilized, the measurement cost can be reduced correspondingly.

Since the movement resistance in the separation film can be reduced, the analytical tool can be structured as a microdevice which utilizes capillary action in a small flow path. In this case, one or a plurality of flow paths may have a principal, rectangular cross section which has a width of 10~500 μm and a depth of 5~500 μm and which satisfies depth/width 0.5. The "principal cross section" herein indicates a vertical section extending perpendicularly to the travel direction of the sample liquid, and indicates the vertical section of a portion which is mainly utilized for traveling the sample liquid when the sectional configuration is not uniform.

Preferably, to promote the movement of the sample liquid through the flow path, one or plurality of flow paths may have a hydrophilically-treated inner surface. The hydrophilization may be so performed that the contact angle of pure water at the inner surface becomes 0~80 degrees, and preferably 0~60 degrees.

As the sample liquid, a biochemical sample such as urine or blood may be used, and typically, blood may be used.

For example, the separation film is positioned higher than one or plurality of flow paths. With such an arrangement, the sample liquid can be moved in the thickness direction of the separation film so that solid components can be removed at the separation film. For example, the analytical tool may further comprise a liquid receiving portion for retaining the sample liquid passed through the separation film, and the liquid receiving portion communicates with the liquid introduction port and one or plurality of flow paths. Preferably, in this case, the separation film is spaced from the bottom surface of the liquid receiving portion.

For example, the analytical tool of the present invention may comprise a substrate in which the liquid receiving portion is formed, a cover in which the liquid introduction port is formed, and an adhesive layer interposed between the substrate and the cover and including a through-hole for fitting the separation film.

When the analytical tool includes a plurality of flow paths, it is preferable that the flow paths extend radially from the liquid receiving portion.

The separation film may be selected depending on the size of a solid component to be removed, and for example, a porous material may be used. Examples of porous material which is usable as the separation film include paper, foam (expanded material), a woven material, a non-woven material, a knitted material, a membrane filter, a glass filter, or a gel material. When the sample liquid is blood and blood cells in the blood are to be separated at the separation film, it is preferable to use, as the separation film, a material whose minimum pore diameter (pore size) is 0.1~3.0 μm.

For example, the analytical tool may comprise reagent portions for reaction with the sample liquid, and a plurality of flow paths for moving the sample liquid. In this case, the reagent portions provided in at least two of the flow paths are different from each other in reagent included therein. In this case, the tool is adapted to measure a plurality of items from a single kind of sample liquid. Preferably, the reagent portions of the at least two flow paths are arranged on a common circle.

Preferably, each of the flow paths is structured to temporarily retain the sample liquid upstream from the reagent portion before the sample liquid is introduced to the reagent portion. Specifically, the analytical tool further comprises a branching flow path branched from a channel set in the flow path. The sample liquid is temporarily retained at the channel in the flow path by bringing the branching flow path into communication with the outside through a portion other than the liquid introduction port, and the sample liquid is caused to move through the flow path beyond the channel by bringing the flow path into communication with the outside through a portion other than the liquid introduction port. Preferably, the flow path is connected to a gas discharge port for discharging gas from the flow path, and the sample liquid is caused to move beyond the channel by opening the gas discharge port.

BEST MODE FOR CARRYING OUT THE INVENTION

Figure 1:
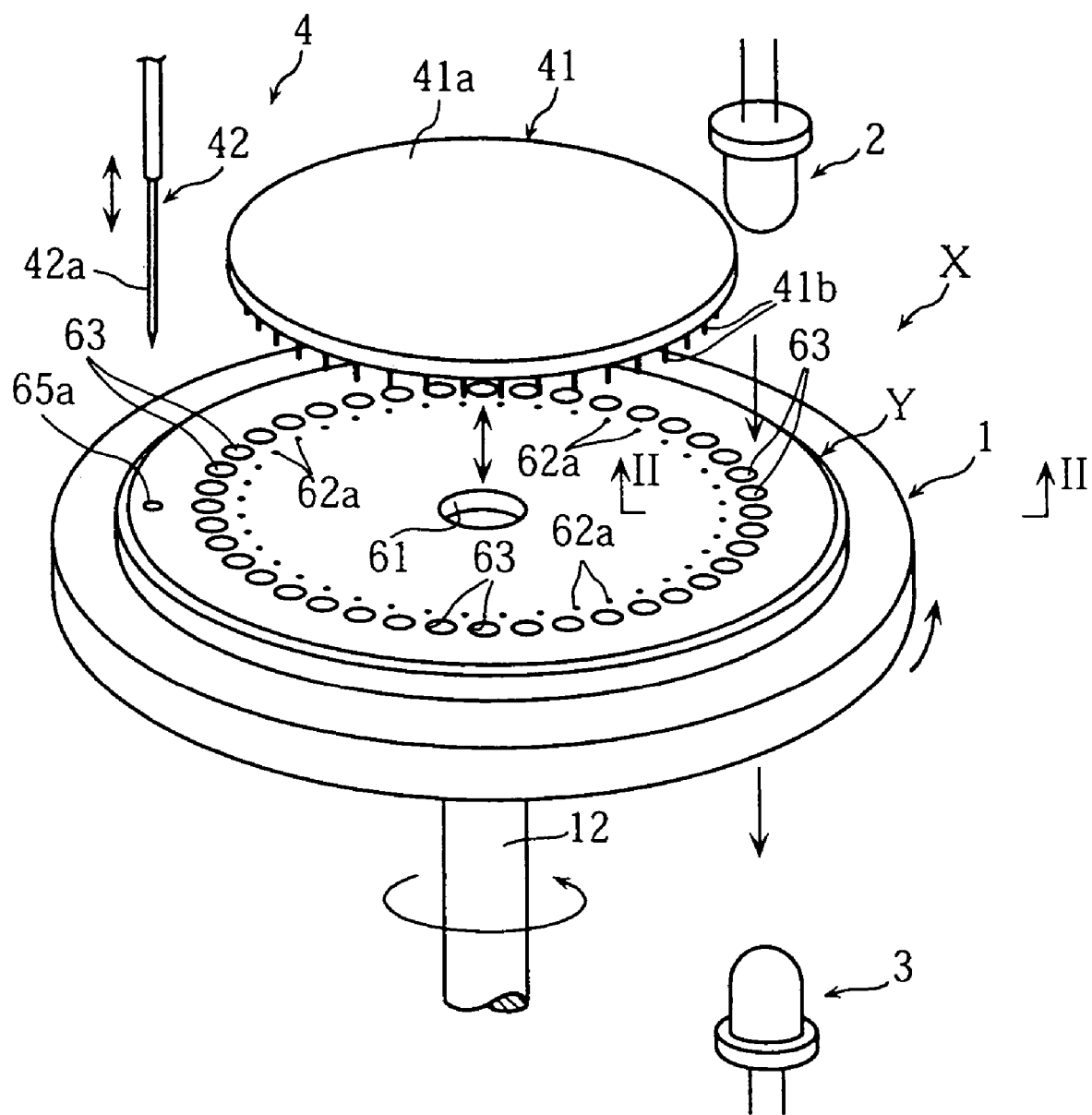
FIG. 1 is a schematic view showing the structure of an example of analytical apparatus and analytical tool according to the present invention.
Figure 2:
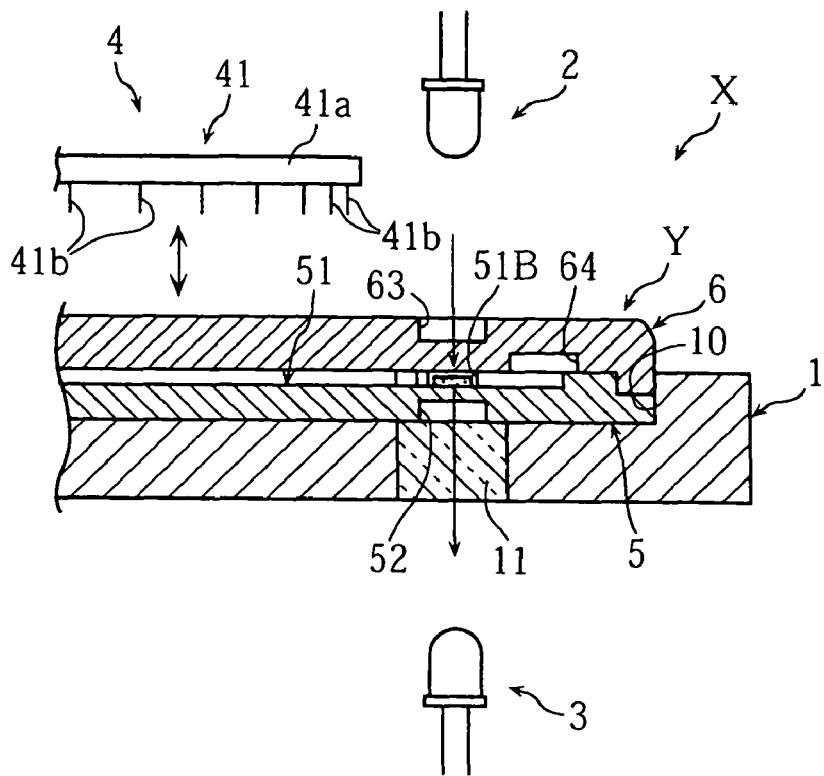
FIG. 2 is a sectional view taken along lines II-II in FIG. 1.

FIGS. 1 and 2 show an analytical apparatus X to which a microdevice Y as an analytical tool is mounted for analyzing a sample liquid. The apparatus includes a mount portion 1 to which the microdevice Y is to be mounted, a light source 2, a light receiving portion 3 and an opening mechanism 4.

Figure 3:
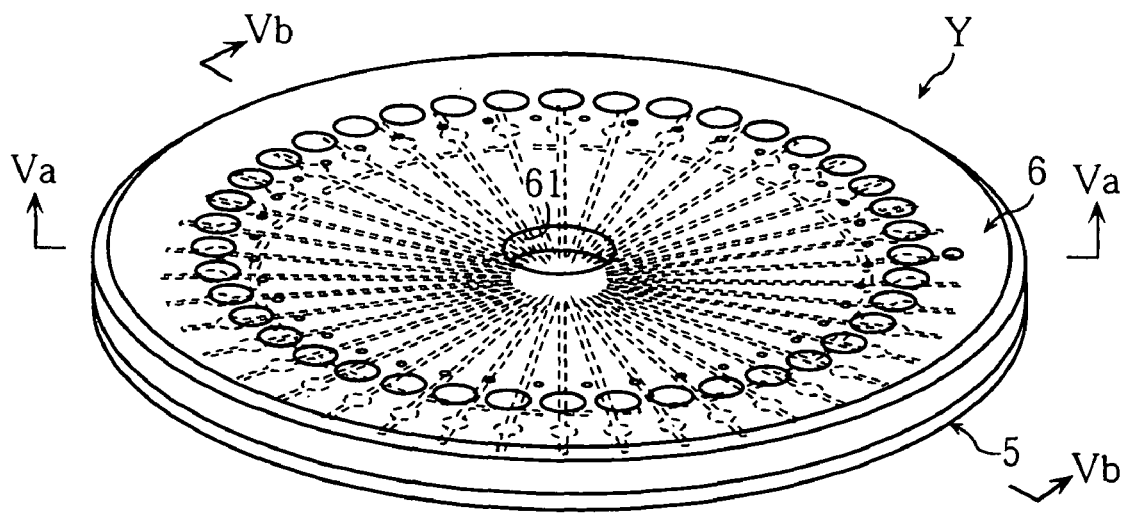
FIG. 3 is an entire perspective view of the microdevice shown in FIG. 1.
Figure 4:
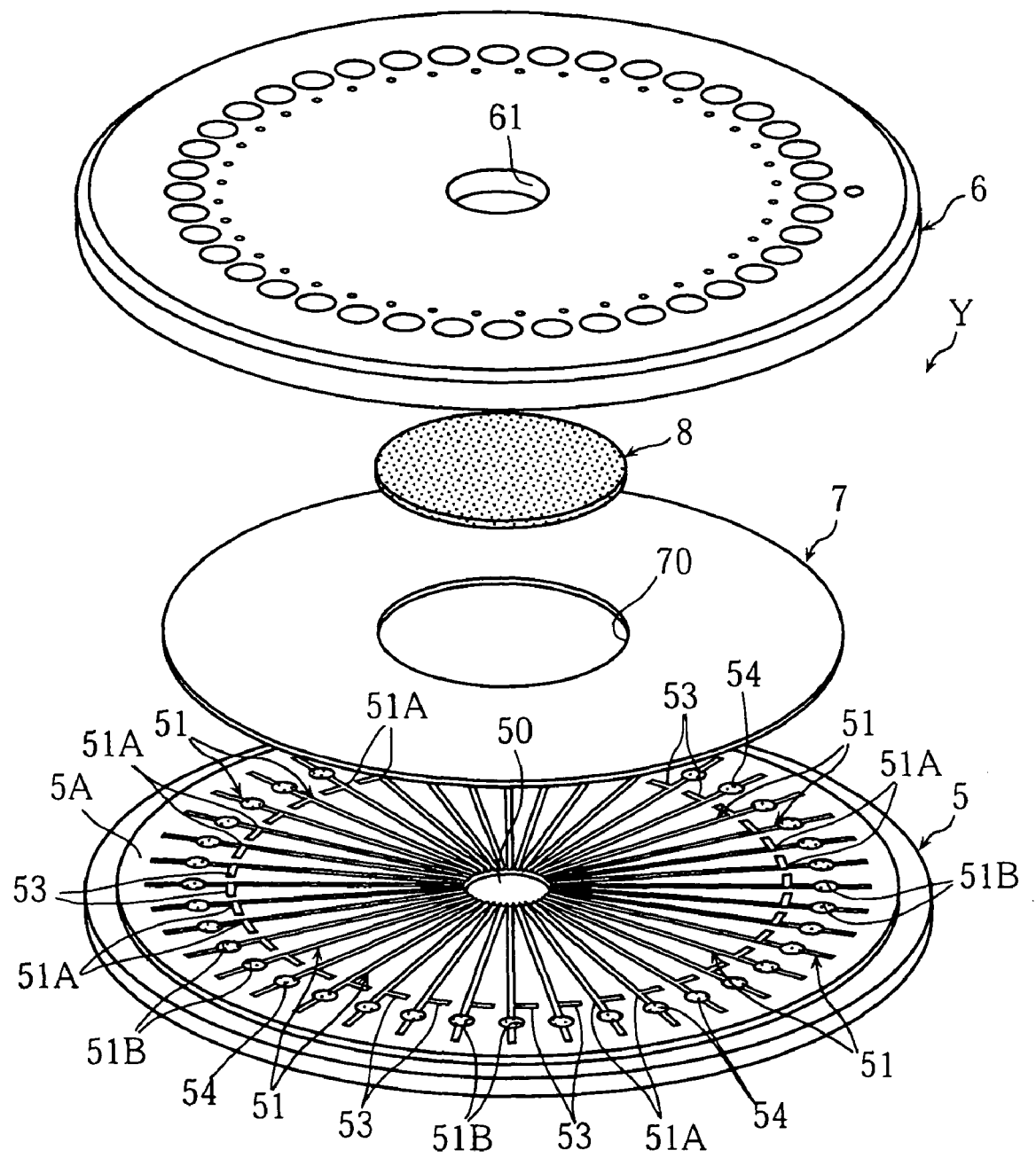
FIG. 4 is an exploded perspective view of the microdevice shown in FIG. 3.

As better shown in FIGS. 3 through 5, the microdevice Y, which serves to provide a reaction field, includes a substrate 5, a cover 6, an adhesive layer 7 and a separation film 8.

Figure 5A:
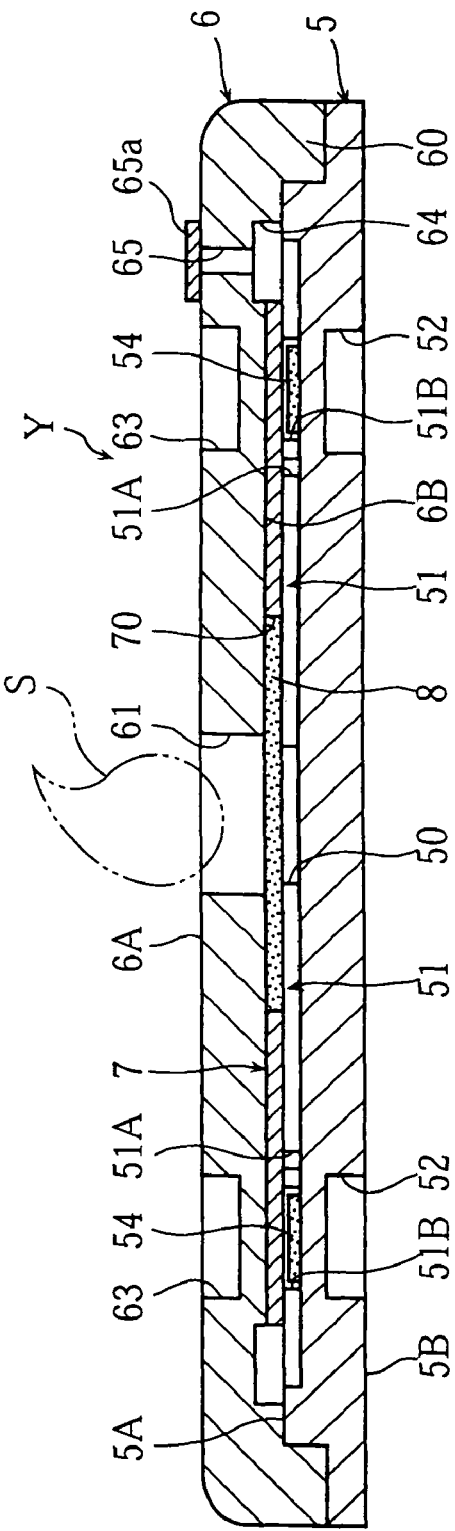
FIG. 5A is a sectional view taken along lines Va-Va in FIG. 3.
Figure 5B:
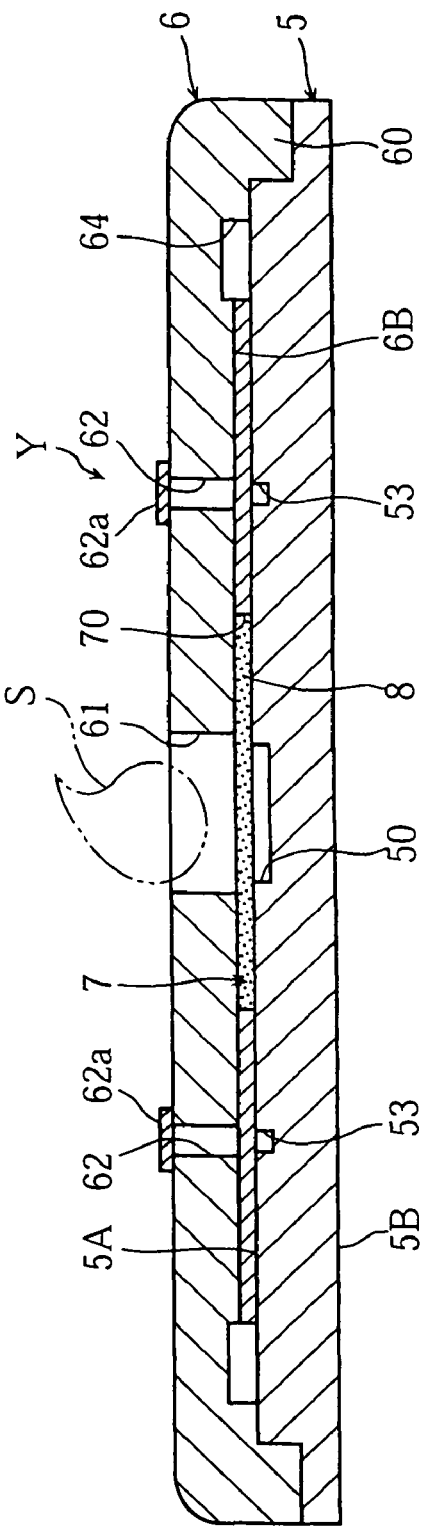
FIG. 5B is a sectional view taken along lines Vb-Vb in FIG. 3.
Figure 6:
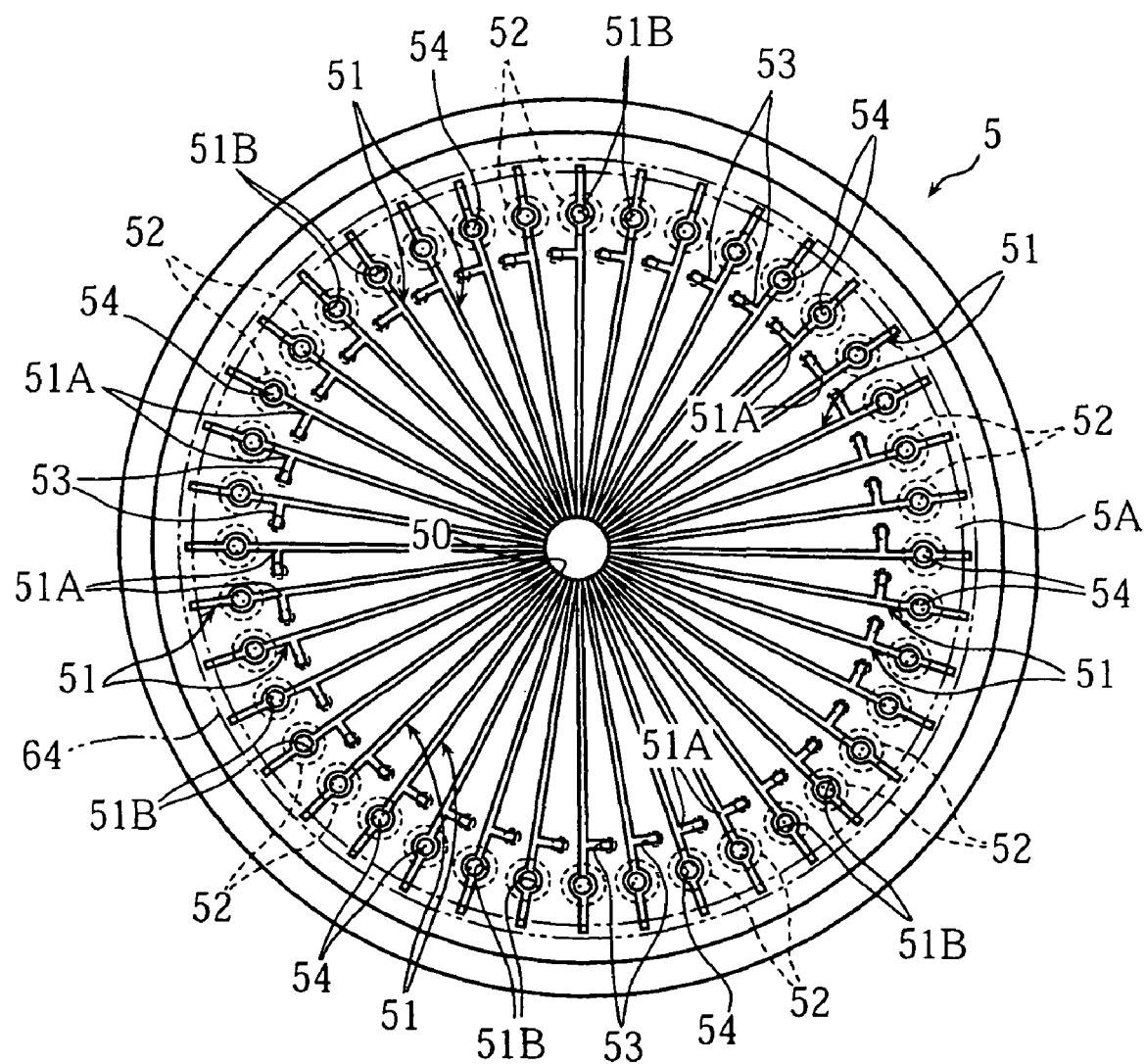
FIG. 6 is a plan view showing a substrate of the microdevice.

The substrate 5 comprises a transparent circular disk having a circumferential edge which is stepped downwardly. As shown in FIGS. 5A and 6, the substrate 5 includes a liquid receiving portion 50 formed at the center thereof, a plurality of flow paths 51 communicating with the liquid receiving portion 50 and extending radially from the liquid receiving portion 50 toward the circumferential edge of the substrate 4, a plurality of recesses 52 and a plurality of branching flow paths 53.

The liquid receiving portion 50 serves to retain a sample liquid supplied to the microdevice Y for introduction to each of the flow paths 51. The liquid receiving portion 50 comprises a circular recess formed on an upper surface 5A of the substrate 5.

Each of the flow paths 51 serves to move the sample liquid and is formed on the upper surface 5A of the substrate 5 so as to communicate with the liquid receiving portion 50. As shown in FIG. 5A, each flow path 51 includes a channel 51A and a reaction portion 51B. The flow path 51 has a generally uniform rectangular cross section except for the reaction portion 51B. For example, the width and depth of the rectangular cross section of the flow path 51 are set to 10~500 μm and 5~500 μm, respectively, and set so that the depth/width ratio is no smaller than 0.5.

As shown in FIGS. 4 and 6, from the channel 51A extends the branching flow path 53 communicating with the flow path 51. The branching flow path 53 is provided as close to the reaction portion 51B as possible so that the distance between the branching flow path 53 and the reaction portion 51B becomes as small as possible. The branching flow path 53 has a generally uniform rectangular cross section of a dimension similar to the rectangular cross section of the flow path.

Each of the reaction portions 51B has a sectional area which is larger than that of the principal cross section of the flow path 51. The reaction portions 51B are arranged on a common circle. As shown in FIG. 5A, each of the reaction portions 51B is provided with a reagent portion 54. However, the reagent portion 54 need not necessarily be provided at every flow path 51. For example, a reagent portion may not be provided with respect to a flow path that is used for correcting the influence of the color of a sample liquid.

The reagent portion 54 comprises a solid which dissolves when a sample liquid is supplied thereto and exhibits a color upon reacting with a particular component contained in the sample liquid. In this embodiment, a plurality of kinds of reagent portions 54 which differ from each other in components or composition are prepared so that a plurality of items can be measured in the microdevice Y.

Each of the recesses 52 serves to emit a light toward the lower surface 5B side of the substrate 5 when the reaction portion 51B is irradiated with light from the upper surface 5A side of the substrate 5 and the light is transmitted to the recess, as will be described later (See FIGS. 1 and 2). The recess 52 is provided at the lower surface 5B of the substrate 5 at a location corresponding to the reaction portion 51B. Therefore, as shown in FIG. 6, the recesses 52 are arranged on the same circle and adjacent to the circumferential edge of the substrate 5.

For example, the substrate 5 is made by molding a transparent resin material such as acrylic resin such as polymethyl methacrylate (PMMA), or polystyrene (PS), polycarbonate (PC) or polyethylene terephthalate (PET). The liquid receiving portion 50, the flow paths 51, the recesses 52 and the branching flow paths 53 can be made at the same time in the resin-molding process by appropriately designing the configuration of the mold.

Preferably, the inner surfaces of the liquid receiving portion 50, the flow paths 51, the recesses 52 and the branching flow paths 53 are hydrophilically treated. Although various known techniques for hydrophilization can be employed, it is preferable that hydrophilization is performed by bringing a mixed gas containing fluorine gas and oxygen gas into contact with each inner surface and then bringing water or water vapor into contact with the inner surface. Unlike a prior art hydrophilization technique such as ultraviolet irradiation, this method is capable of hydrophilically treating a standing surface (side surface of a flow path, for example) as well, because this method utilizes gas and water for hydrophilization. The hydrophilization with respect to each inner surface is so performed that the contact angle of pure water at the inner surface becomes 0~80 degrees, and preferably 0~60 degrees.

Figure 7:
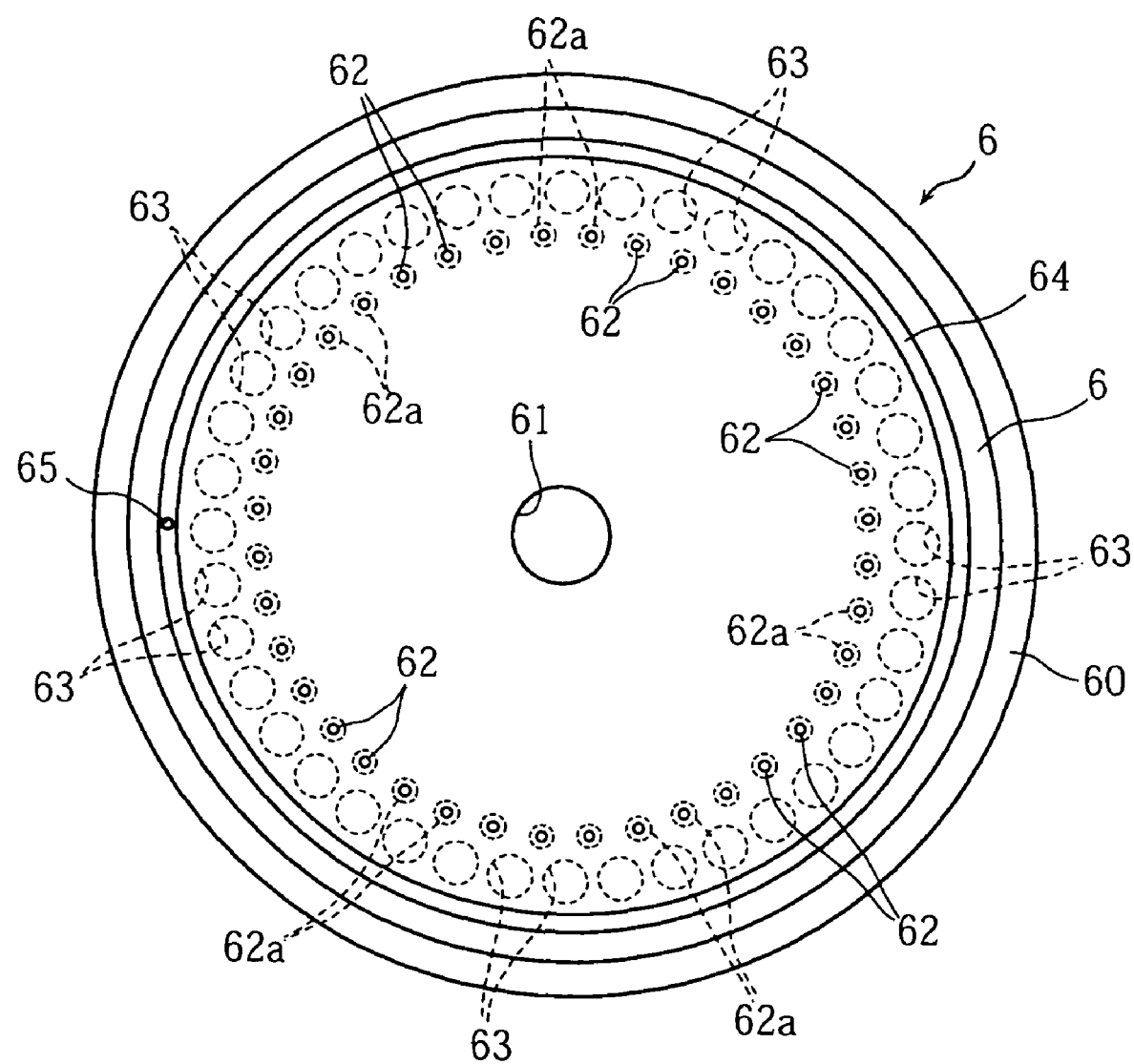
FIG. 7 is a bottom view showing a cover of the microdevice.

The cover 6 is in the form of a circular disk having a downwardly projecting circumferential edge. The projection 60 of the cover 6 serves to engage the stepped, smaller-thickness portion of the substrate 5. As shown in FIGS. 5 and 7, the cover 6 includes a sample introduction port 61, a plurality of first gas discharge ports 62, a plurality of recesses 63, a common flow path 64 and a second gas discharge port 65.

The sample introduction port 61, which is used for introducing a sample liquid, comprises a through-hole. As better shown in FIG. 5, the sample introduction port 61 is provided at the center of the cover 6 and directly above the liquid receiving portion 50 of the substrate 5.

Each of the first gas discharge ports 62, which are used for discharging gas from the flow paths 51, comprises a through-hole. As better shown in FIG. 5B, the first gas discharge ports 62 are provided directly above the branching flow paths 53 of the substrate 5, respectively. As a result, as shown in FIGS. 4 and 7, the first gas discharge ports 62 are arranged on a common circle. As better shown in FIG. 5B, the upper opening of each of the first gas discharge ports 62 is closed by a sealing member 62a. The sealing member 62a may be made of metal such as aluminum or resin. The sealing member 62a is fixed to the substrate 5 by the use of an adhesive or by fusing, for example.

The recesses 63 are utilized for irradiating the reaction portions 51B with light from the upper surface 6A side of the cover 6, as will be described later (See FIGS. 1 and 2). As shown in FIG. 5A, each of the recesses 63 is provided at the upper surface 6A of the cover 6 and directly above the reaction portion 51B. As a result, as shown in FIGS. 4 and 7, the recesses 63 are arranged on a common circle and adjacent to the circumferential edge of the cover 6.

The common flow path 64 serves to guide gas to the second gas discharge port 65 in discharging gas in the fluid paths 51 to the outside. As shown in FIGS. 5 and 7, the common flow path 64 comprises an annular recess provided at a peripheral portion of the lower surface 6B of the cover 6. As shown in FIGS. 5A and 6, the common flow path 64 communicates with the flow paths 51 of the substrate 5.

As shown in FIGS. 5A and 7, the second gas discharge port 65 comprises a through-hole communicating with the common flow path 64. The upper opening of the second gas discharge port 65 is closed by a sealing member 65a. As the sealing member 65a, use may be made of one that is similar to the sealing member 62a.

Similarly to the substrate 5, the cover 6 may be made by resin-molding using a transparent resin material. The sample introduction port 61, the first gas discharge ports 62, the recesses 63, the common flow path 64 and the second gas discharge port 65 can be made at the same time in the resin-molding process. It is preferable that the cover 6 as well is hydrophilically treated at least at the portion facing the flow paths 51 of the substrate 5. The hydrophilization can be performed by the same technique as that for the substrate 5.

As better shown in FIG. 5, the adhesive layer 7 serves to bond the cover 6 to the substrate 5. As shown in FIGS. 4 and 5, the adhesive layer 7 is provided by interposing an adhesive sheet, which is formed with a through-hole 70 at the center thereof, between the substrate 5 and the cover 6. The through-hole 70 of the adhesive layer 7 has a diameter which is larger than those of the liquid receiving portion 50 of the substrate 5 and the sample introduction port 61 of the cover 6. The adhesive sheet may be made by forming adhesive layers at opposite surfaces of a base material.

The separation film 8 serves to separate solid components contained in a sample liquid such as blood cells in blood. As shown in FIG. 5, the separation film 5 has a diameter corresponding to the diameter of the through-hole 70 of the adhesive layer 7 and is fitted into the through-hole 70 of the adhesive layer 7 to intervene between the liquid receiving portion 50 of the substrate 5 and the sample introduction port 61 of the cover 6. Since the liquid receiving portion 50 comprises a recess, the separation film 8 is spaced from the bottom surface of the liquid receiving portion 50. Since the diameter of the separation film 8 corresponds to the diameter of the through-hole 70 which is larger than that of the liquid receiving portion 50, each of the flow paths 51 is covered by the separation film 8 at a portion which is close to the liquid receiving portion 50. By such an arrangement of the separation film 8, the sample liquid introduced through the sample introduction port 61 passes through the separation film 8 in the thickness direction and then reaches the liquid receiving portion 50.

As the separation film 8, a porous material may be used, for example. Examples of porous material used as the separation film 8 includes paper, foam (expanded material), an woven material, a non-woven material, a knitted material, a membrane filter, a glass filter, or a gel material. When the sample liquid is blood and blood cells in the blood are to be separated in the separation film 8, it is preferable to use, as the separation film 8, a material whose minimum pore diameter (pore size) is 0.1~3.0 µm.

The mount portion 1 shown in FIGS. 1 and 2 includes a recess 10 for holding the microdevice Y. In the mount portion 1 is defined a light transmitting region 11. The light transmitting region 11 is provided at a location which corresponds to the reaction portion 51B when the microdevice Y is mounted to the recess 10. The light transmitting portion 11 is provided by forming the relevant region of the mount portion 1 by using a transparent material such as transparent resin. Alternatively, the mount portion 1 may be entirely made of a transparent material. The mount portion 1 is supported by a rotation shaft 12 so that the mount portion 1 rotates in accordance with the rotation of the rotation shaft 12. The rotation shaft 12 is connected to a non-illustrated driving mechanism and is controlled to rotate by a predetermined angle corresponding to the arrangement pitch of the reaction portions 51B of the microdevice Y.

The light source 2 serves to irradiate the reaction portions 51B of the microdevice Y with light and is fixed at a position for facing the recesses 63 of the cover 6. The light source 2 may comprise a mercury lamp or a white LED, for example. Though not illustrated, when such a light source is used, the light from the light source 2 is caused to pass through a filter before reaching the reaction portions 51B. By using such a filter, it is possible to select a light of an appropriate wavelength in accordance with the light absorption characteristics of the substance as an object to be analyzed contained in the reaction liquid.

The light receiving portion 3 serves to receive light passed through the reaction portion 51B and is fixed at a position for facing the recesses 52 of the substrate 5. The amount of light received by the light receiving portion 3 is used as the base for the analysis of the sample liquid (for the concentration computation, for example). The light receiving portion 3 may comprise a photodiode, for example.

The opening mechanism 4 includes a first hole-making member 41 for making a hole in the seal portion 62a, and a second hole-making member 42 for making a hole in the seal portion 65a. The hole-making members 41 and 42 are reciprocally movable up and down by the operation of a non-illustrated actuator.

Figure 8:
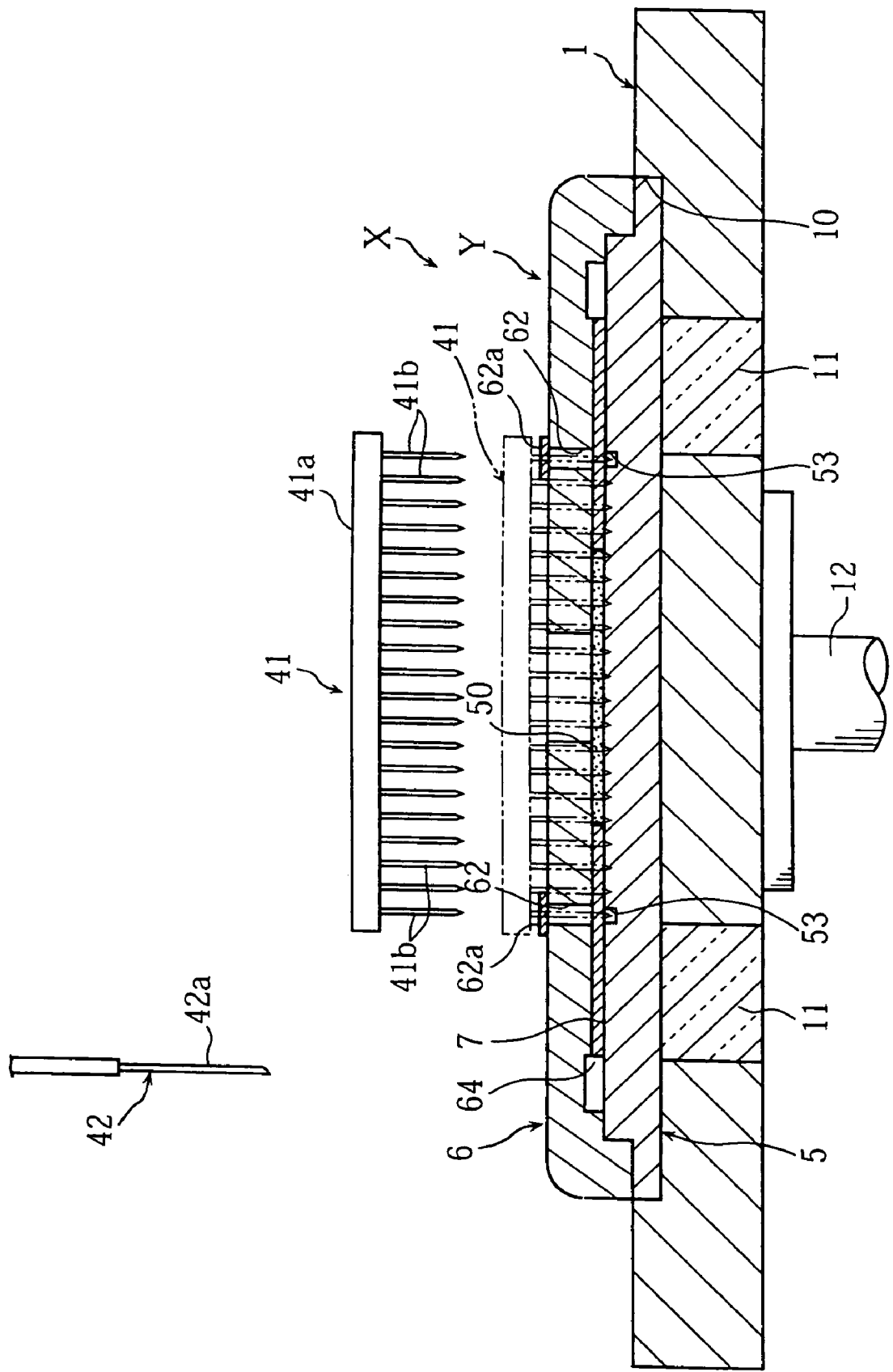
FIG. 8 is a sectional view showing the operation for opening first gas discharge ports.

The first hole-making member 41 includes a substrate 41a in the form of a circular disk, and a plurality of needles 41b projecting downward from the lower surface of the substrate. As shown in FIG. 8, each of the needles 41b has a diameter which is smaller than that of the first gas discharge ports 62 of the cover 6. The needles 41b are arranged on a common circle and at a pitch corresponding to the pitch of the first gas discharge ports 62. Therefore, when the first hole-making member 41 is moved downward with the needles 41b positioned to face the first gas discharge ports 62, respectively, holes can be made simultaneously with respect to the plurality of seal portions 62a. By this operation, each of the first gas discharge ports 62 opens, whereby the interior of each flow path 51 is brought into communication with the outside through the branching flow path 53 and the first gas discharge port 62.

Figure 9:
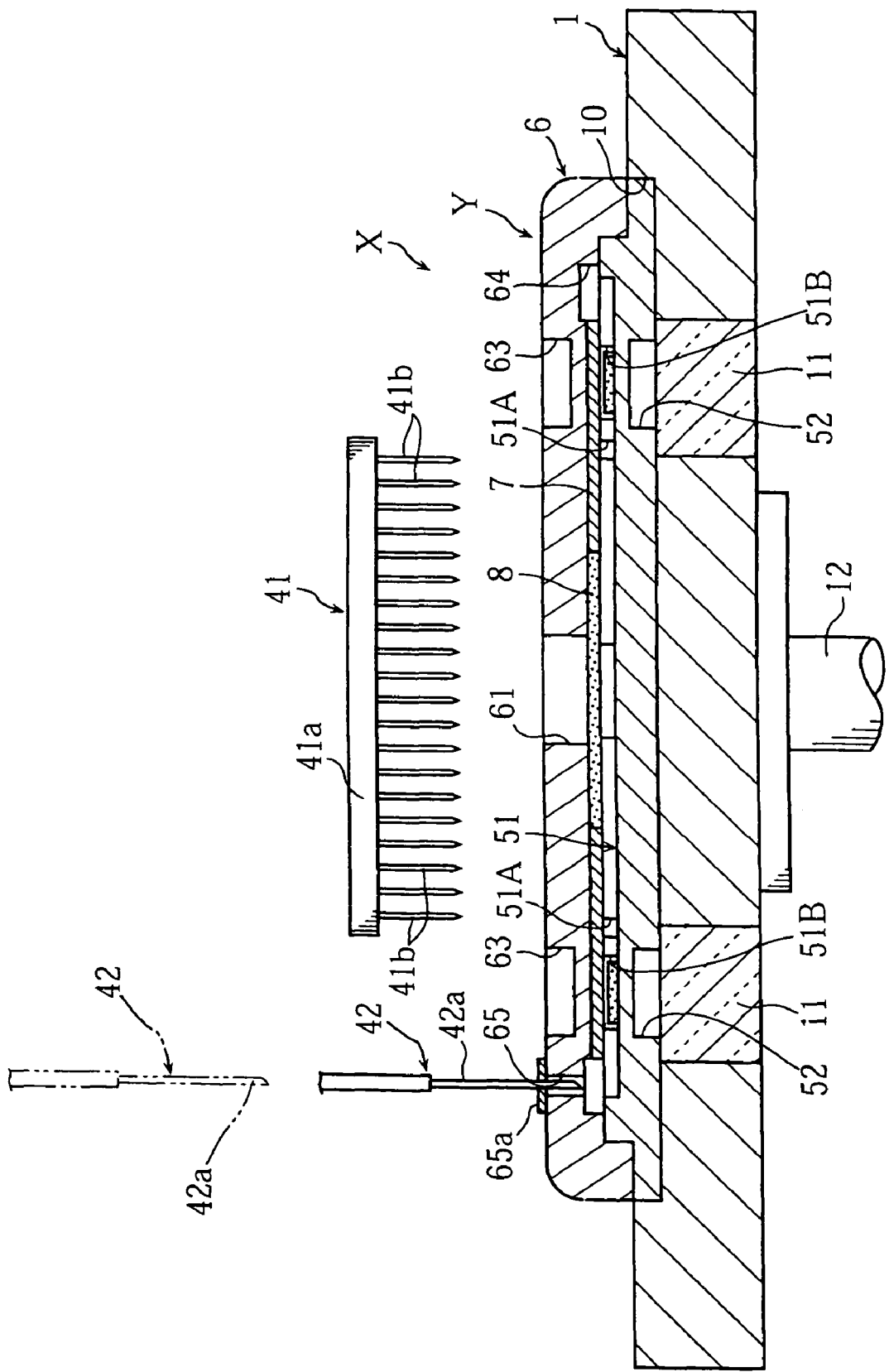
FIG. 9 is a sectional view showing the operation for opening a second gas discharge port.

As shown in FIGS. 1 and 9, the second hole-making member 42 includes a needle 42a. The needle 42a has a diameter which is smaller than that of the second gas discharge port 65 of the cover 6. Therefore, when the second hole-making member 42 is moved downward with the needle 42a of the second hole-making member 42 positioned to face the second gas discharge port 65 of the cover 6, a hole is made in the seal portion 65a. By this operation, the second gas discharge port 65 opens, whereby the interior of each flow path 51 is brought into communication with the outside through the common flow path 64 and the second gas discharge port 65.

The method for opening the first and the second gas discharge ports 62, 65 is not limited to those described above. For example, the first and the second gas discharge ports 62, 65 may be opened by melting or deforming the sealing members 62a, 65a by applying energy to the sealing members 62a, 65a. The energy application may be performed by using a light source such as a laser, an ultrasonic generator or a heating element, for example. Alternatively, the gas discharge ports 62, 65 may be opened by peeling off the sealing members 62a, 65a.

For analyzing a sample liquid, the sample liquid S is supplied to the microdevice Y through the sample introduction port 61. The supply of the sample liquid S may be performed after the microdevice Y is mounted to the analytical apparatus X. However, it is preferable that the microdevice Y is mounted to the analytical apparatus X after the sample liquid S is supplied to the microdevice Y.

Figure 10A:
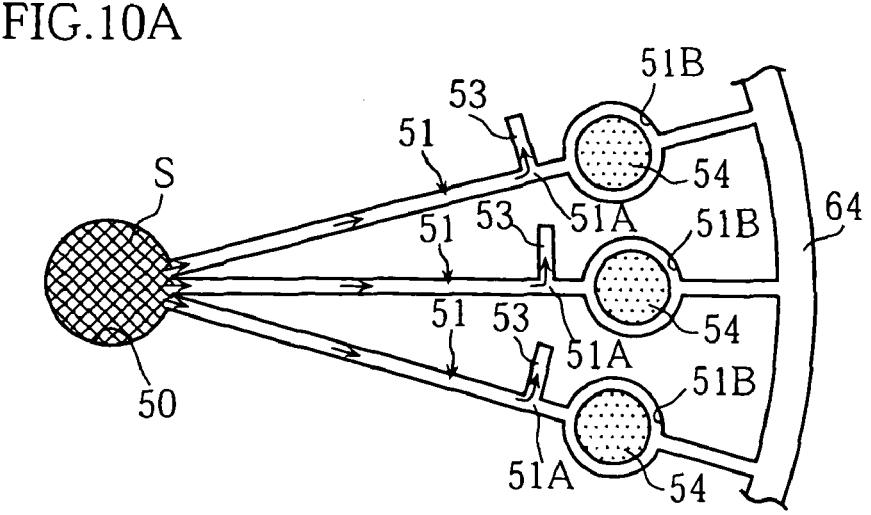
FIG. 10 is a schematic view showing the movement of a sample liquid through flow paths.

As will be understood from FIG. 5, when the sample liquid S is supplied to the microdevice Y, the sample liquid S passes through the separation film 8 in the thickness direction of the film to reach the liquid receiving portion 50. At this time, solid components are removed from the sample liquid S. For example, when blood is used as the sample liquid, blood cells are removed from the blood. Since the first and the second gas discharge ports 62, 65 are closed in supplying the sample liquid S, the sample liquid S is retained in the liquid receiving portion 50 and does not flow into the flow paths 51, as schematically shown in FIG. 10A.

In this embodiment, solid components are removed by moving the sample liquid in the thickness direction of the separation film 8. Therefore, as compared with the structure in which solid components are removed by moving the sample liquid in the plane direction of the separation film 8, the retention time of the sample liquid in the separation film 8 becomes shorter. Therefore, the time necessary for removing solid components becomes shorter.

To introduce the sample liquid S to the flow paths 51, holes are made simultaneously with respect to the plurality of seal portions 62a. As shown in FIG. 8, the making of holes in the seal portions 62a is performed by moving the first hole-making member 41 downward to insert the needles 41b into the seal portions 62a and then moving the first hole-making member 41 upward to remove the needles 41b from the seal portions 62a. By this operation, holes are made simultaneously with respect to the plurality of seal portions 62a. The upward and downward movement of the first hole-making member 41 may be performed automatically in the analytical apparatus X by the user's operation of an operation switch, for example.

Figure 10B:
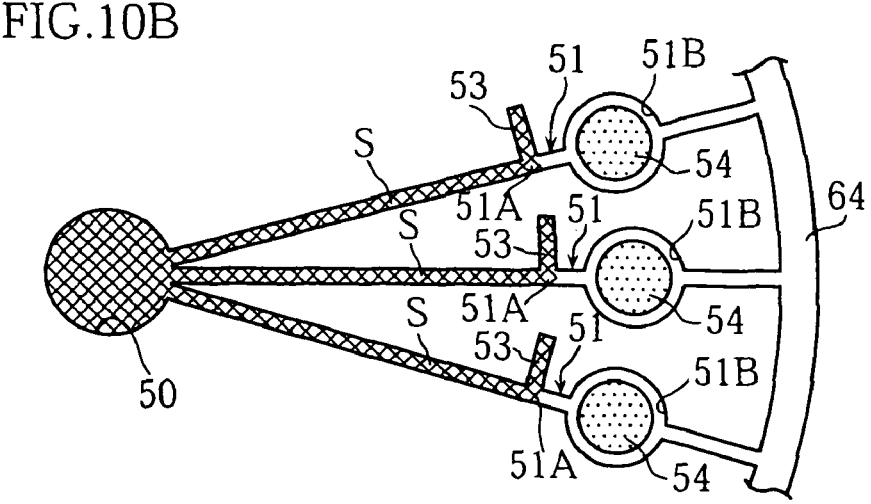

When the holes are made at the seal portions 62a, the interior of the flow paths 51 are brought into communication with the outside through the first gas discharge ports 62 and the branching flow paths 53. Therefore, the sample liquid S retained in the liquid receiving portion 50 moves through the flow paths 51 by capillary action. As indicated by arrows in FIG. 10A, when the sample liquid S reaches each channel 51A, the sample liquid S cannot move beyond the channel 51A to reach the reaction portion 51B and is guided to the branching flow path 53. As a result, as schematically shown in FIG. 10B, the sample liquid S is retained in close proximity to the reaction portion 51B. Thus, the preparation for the reaction of the sample liquid S with the reagent at the reaction portion 51B is completed.

To guide the sample liquid s to the reaction portion 51B, a hole is made at the seal portion 65a. As shown in FIG. 9, the making of a hole at the seal portion 65a is performed by moving the second hole-making member 42 downward to insert the needle 42a into the seal portion 65a and then moving the second hole-making member 42 upward to remove the needle 42a from the seal portion 65a. The upward and downward movement of the second hole-making member 42 may be performed automatically in the analytical apparatus X by the user's operation of an operation switch, for example.

Figure 10C:
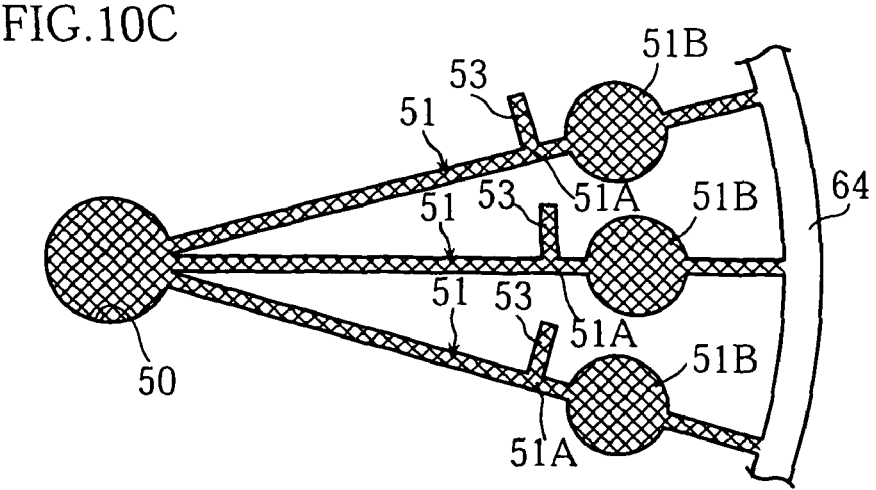

When the hole is made at the seal portion 65a, the interior of each flow path 51 is brought into communication with the outside through the second gas discharge port 65 and the common flow path 64. Therefore, the sample liquid S, which has stopped upstream from the reaction portion 51B, moves again through the flow path 51 by capillary action. Thus, as shown in FIG. 10C, the sample liquid S moves beyond the channel 51A in each flow path 51, whereby the sample liquid S is supplied collectively to the plurality of reaction portions 51.

At each of the reaction portions 51B, the reagent portion 54 is dissolved by the sample liquid to establish a liquid phase reaction system. As the sample liquid S reacts with the reagent, the liquid phase reaction system exhibits a color depending on the amount of the substance to be detected in the sample or a reaction product is produced in accordance with the amount of the substance to be detected. As a result, the liquid phase reaction system of the reaction portion 51B exhibits light transmission characteristics (light absorption characteristics) depending on the amount of the substance to be detected. When a predetermined time period has elapsed from the sample supply to the reaction portion 51B, the reaction portion 51B is irradiated with light from the light source 2 shown in FIGS. 1 and 2, and the amount of transmitted light is measured at the light receiving portion 3. The light irradiation by the light source 2 and the light receiving at the light receiving portion 3 are performed with respect to each of the reaction portions 51B of the flow paths 51 by turning the mount portion 1 by a predetermined angle. In the analytical apparatus X, the analysis of the sample, e.g. the computation of the concentration of a substance to be detected, is performed based on the amount of light received at the light receiving portion 3.

In the above-described analysis method, after the sample liquid S is guided to a portion (each channel 51A) close to the reaction portion 51B, the sample liquid S is supplied from the channel 51A to the reaction portion 51B by opening the seal portion 65a. Thus, the sample liquid S can be supplied to the reaction portions 51B of the plurality of flow paths 51 just by opening a single gas discharge port. Therefore, the time taken from when the operation to supply the sample liquid S is performed (the seal portion 65a is opened) until when the sample liquid reaches the reaction portions 51B can be shortened. Accordingly, variation of the time taken from the sample supply starting operation to the completion of the sample supply among the flow paths 51 and among each measurement (among analytical tools) can be reduced. Thus, the timing at which the reaction starts at the reaction portions 51 can be properly controlled by the operation of opening the seal portion 65a. Particularly, in this embodiment, the sample liquid can be supplied simultaneously to the plurality of reaction portions 51B just by opening a single gas discharge port. Therefore, it is possible to make the reaction time uniform among the reaction portions 51B and among a plurality of microdevices Y, whereby the measurement error can be reduced.

Figure 11:
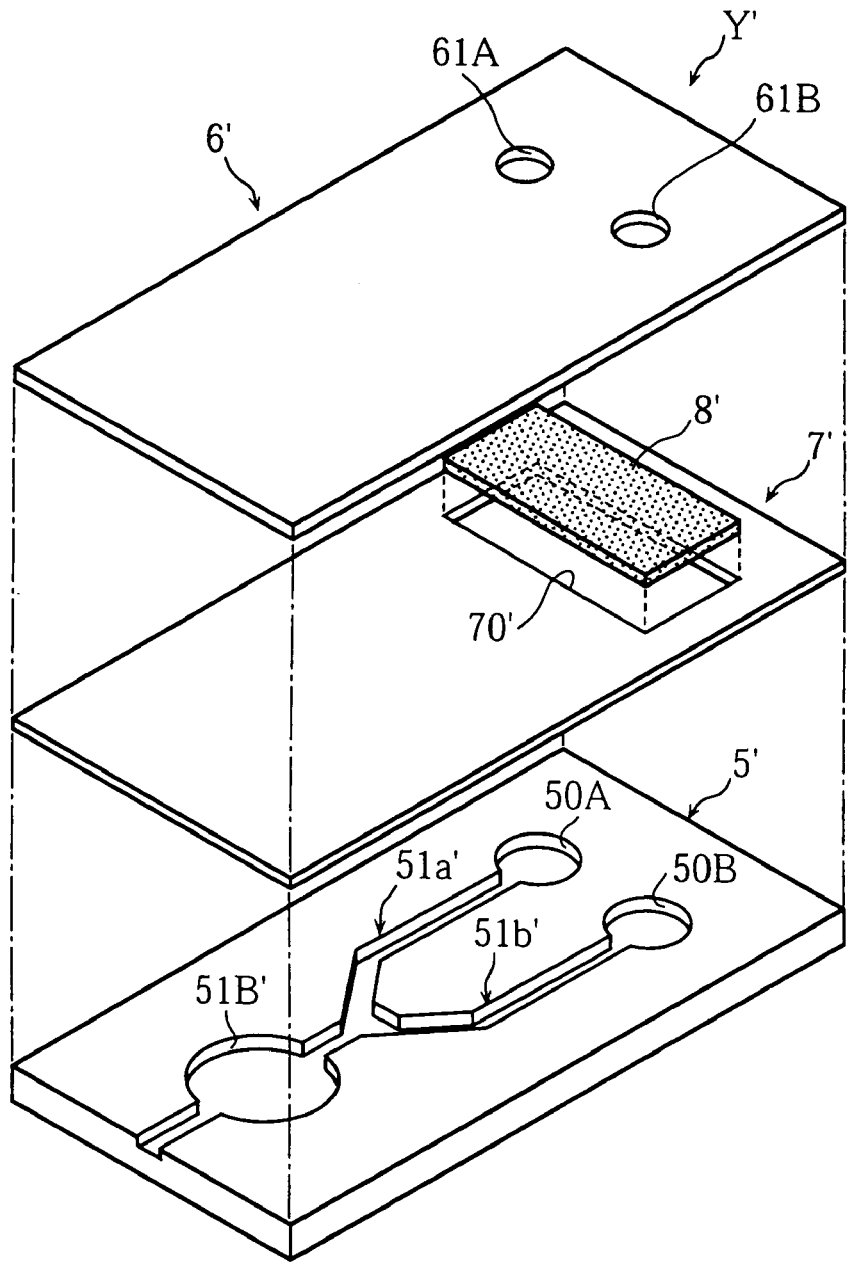
FIG. 11 is an exploded perspective view showing another example of microdevice according to the present invention.
Figure 12:
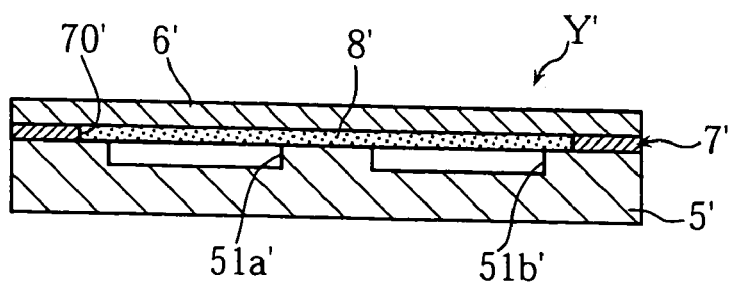
FIG. 12 is a sectional view of the microdevice shown in FIG. 11.
Figure 13:
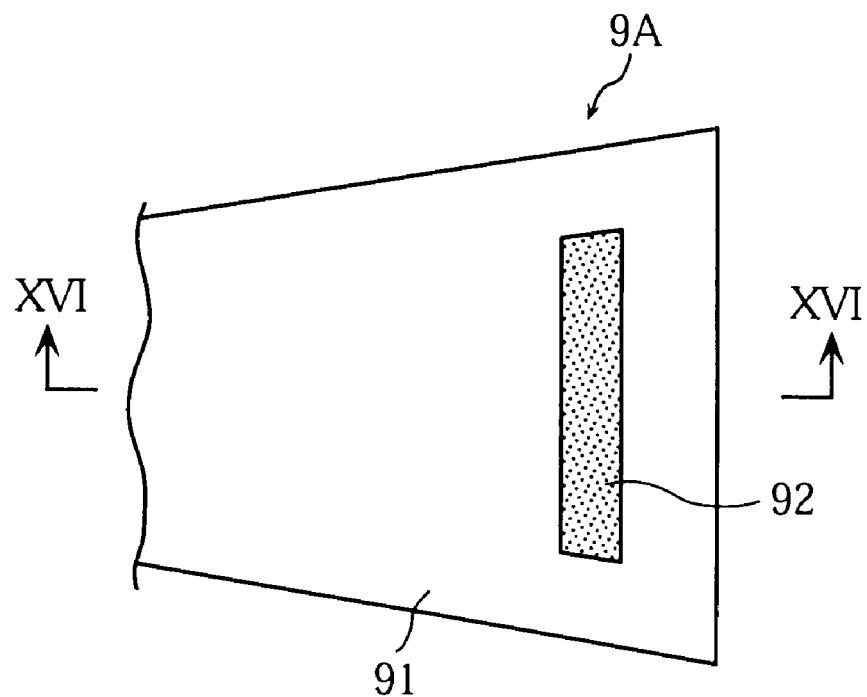
FIG. 13 is a plan view showing a principal portion of a prior art analytical tool.
Figure 14:
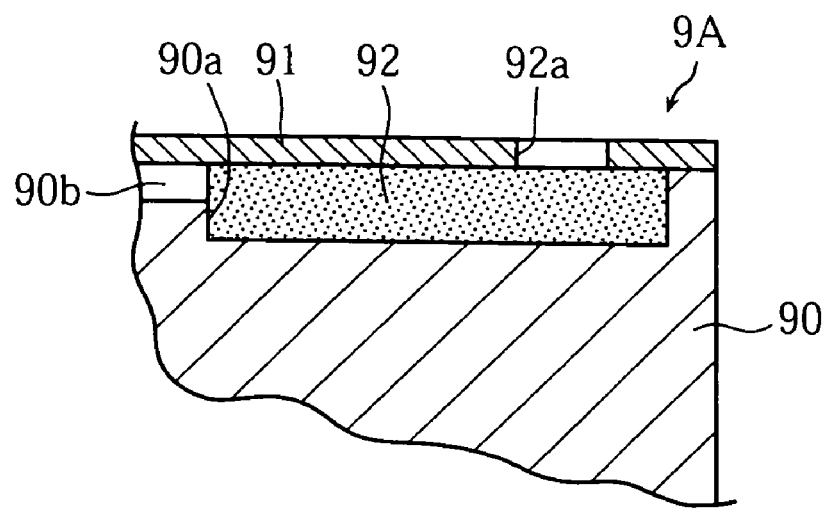
FIG. 14 is a sectional view taken along lines XVI-XVI in FIG. 13.
Figure 15:
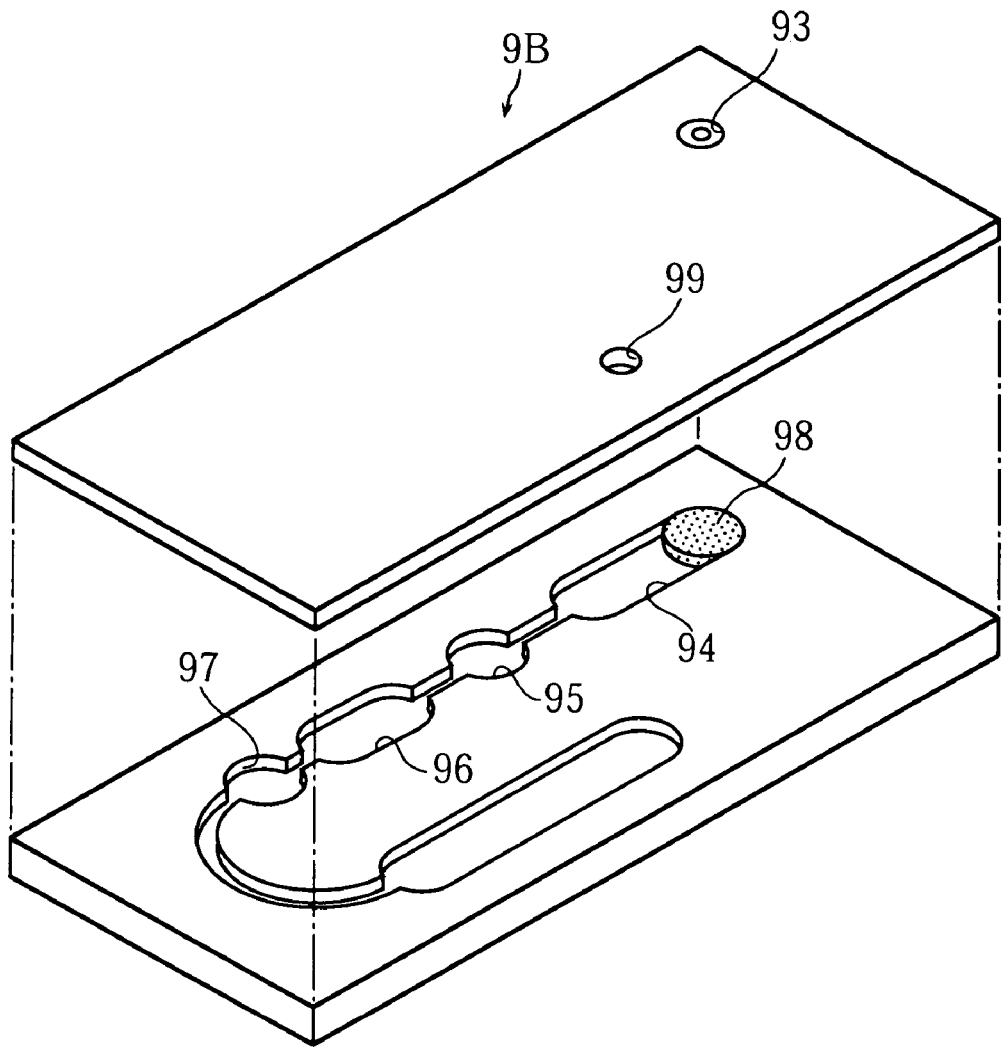
FIG. 15 is an exploded perspective view showing another example of prior art analytical tool.
Figure 16:
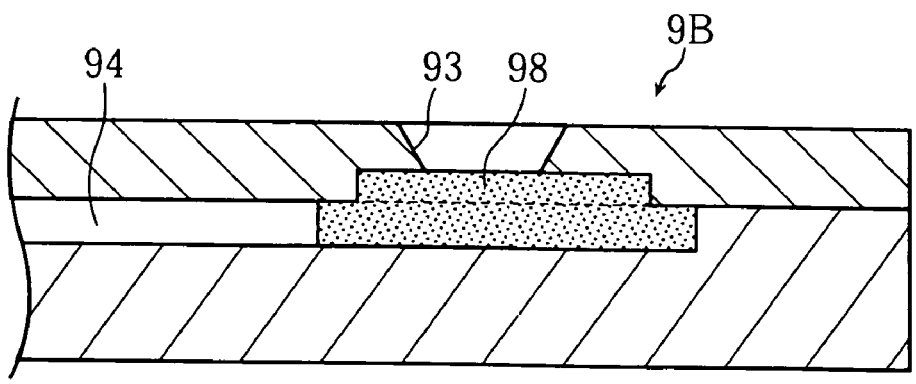
FIG. 16 is a sectional view showing a principal portion of the analytical tool shown in FIG. 15.

The present invention is not limited to the foregoing embodiments and may be modified in various ways. For example, the present invention is applicable to such a microdevice as shown in FIGS. 11 and 12, which includes a plurality of sample introduction ports. The microdevice Y' shown in the figures includes a substrate 5', and a cover 6' bonded to the substrate via an adhesive sheet 7'. The substrate 5' includes a sample flow path 51a' and a reagent flow path 51b' respectively provided with liquid receiving portions 50A and 50B at the ends thereof, and a reaction portion 51B' for causing reaction between the sample liquid and the reagent liquid. The cover 6' includes a sample introduction port 61A and a reagent introduction port 61B. The adhesive sheet 7' includes an opening 70' formed to expose the two liquid receiving portions 50A and 50B. In the opening 70' is fitted a separation film 8'.

In the analytical tool Y', the sample liquid and the reagent liquid respectively supplied through the sample introduction port 61A and the reagent introduction port 61B move in the thickness direction of the separation film 8' to reach the liquid receiving portions 50A and 60B. Thereafter, the sample liquid and the reagent liquid move to the reaction portion 51B' by capillary action and undergo reaction at the reaction portion 51B'. The reaction product is analyzed by an optical method.

In the analytical tool Y' shown in FIGS. 11 and 12, the separation film 8' is arranged to collectively cover the two liquid receiving portions 50A and 50B. However, a separation film may be arranged for each of the liquid receiving portions 50A and 50B.

Although the analysis based on the light which is transmitted when the reaction portion is irradiated with light is described in the foregoing embodiments, the present invention is also applicable to the sample analysis based on the light reflected from the reaction portion. The irradiation of the reaction portion and the measurement of the transmitted light need not necessarily be performed individually with respect to each reaction portion but may be performed collectively with respect to the plurality of reaction portions.

The present invention is applicable to an analytical tool which is designed to move a mobile component by capillary action. Therefore, the invention is applicable to a tool for performing analysis by an electrochemical method as well as that for performing analysis by an optical method. Moreover, the invention is applicable not only to an analysis method in which a sample is moved but also to an analysis method in which a reagent is moved instead of a sample and a method in which a sample and a reagent are moved together with a carrier liquid. The application of the present invention is not limited to microdevices, and the invention is also applicable to other types of analytical tools.

The invention claimed is:

1. An analytical tool comprising:
   a liquid introduction port,
   at least one flow path for moving a sample liquid introduced through the liquid introduction port,
   a reaction chamber communicating with said at least one flow path, and
   a separation film disposed below the liquid introduction port and above said at least one flow path for filtering the sample liquid supplied to the liquid introduction port before introducing the sample liquid to said at least one flow path;
   wherein the sample liquid is caused to move through the separation film in a thickness direction of the separation film for filtration;

wherein a branching flow path branches from said at least one flow path at a branching position upstream from and close to the reaction chamber;

wherein the branching flow path communicates with a first gas discharge port closed by a first seal film that is openable by needle insertion for supplying the sample liquid from the liquid introduction port to the branching position; and wherein the reaction chamber communicates with a second gas discharge port closed by a second seal film that is openable by needle insertion for supplying the sample liquid beyond the branching position to the reaction chamber.

2. The analytical tool according to claim 1, wherein said at least one flow path moves the sample liquid by capillary action.

3. The analytical tool according to claim 1, wherein the sample liquid comprises blood, and wherein the separation film separates blood cells from the blood.

4. The analytical tool according to claim 3, wherein the separation film comprises a porous film having a minimum pore size of 0.1~3.0 μm.

5. The analytical tool according to claim 1, wherein said at least one flow path extends in a plane that is parallel to the separation film.

6. The analytical tool according to claim 5, further comprising a liquid receiving portion for retaining the sample liquid passed through the separation film, the liquid receiving portion communicating with the liquid introduction port and said at least one flow path, and wherein the separation film is spaced from a bottom surface of the liquid receiving portion.

7. The analytical tool according to claim 6, further comprising:

a substrate in which the liquid receiving portion and said at least one flow path are formed;

a cover in which the liquid introduction port, the first discharge port and the second discharge port are formed; and an adhesive layer interposed between the substrate and the cover, the adhesive layer including a through-hole for fitting the separation film.

8. The analytical tool according to claim 6, wherein said at least one flow path extends radially from the liquid receiving portion.

9. The analytical tool according to claim 1, wherein a plurality of flow paths are provided for communicating with a plurality of reaction chambers, respectively, at least two of the plurality of reaction chambers each containing a different reagent; and wherein the tool is adapted to measure a plurality of items from a single kind of sample liquid.

10. The analytical tool according to claim 9, wherein the plurality of reaction chambers are arranged on a common circle.

11. The analytical tool according to claim 1, wherein said at least one flow path has a principal, rectangular cross section which has a width of 10 to 500 μm and a depth of 5 to 500 μm and which satisfies depth/width$\geq$0.5.

12. The analytical tool according to claim 1, wherein said at least one flow path includes a hydrophilically-treated inner surface.

13. The analytical tool according to claim 12, wherein the inner surface of said at least one flow path is so treated that a contact angle of pure water at the inner surface becomes 0-80 degrees.

14. An analytical tool, comprising:

a liquid introduction port, at least one flow path for moving a sample liquid introduced through the liquid introduction port, a reaction chamber communicating with said at least one flow path, and a separation film disposed below the liquid introduction port and above said at least one flow path for filtering the sample liquid supplied to the liquid introduction port before introducing the sample liquid to said at least one flow path;

wherein the sample liquid is caused to move gravitationally through the separation film in a thickness direction of the separation film for filtration;

wherein a branching flow path branches from said at least one flow path at a branching position upstream from and close to the reaction chamber;

wherein the branching flow path communicates with a first gas discharge port closed by a first seal member which is openable for supplying the sample liquid from the liquid introduction port to the branching position; and wherein the reaction chamber communicates with a second gas discharge port closed by a second seal member which is openable for supplying the sample liquid beyond the branching position to the reaction chamber.

15. An analytical apparatus comprising an analytical tool and a hole-making mechanism, the analytical tool comprising:

a liquid introduction port, at least one flow path for moving a sample liquid introduced through the liquid introduction port, a reaction chamber communicating with said at least one flow path, and a separation film for filtering the sample liquid supplied to the liquid introduction port before introducing the sample liquid to said at least one flow path;

wherein the sample liquid is caused to move through the separation film in a thickness direction of the separation film for filtration;

wherein a branching flow path branches from said at least one flow path at a branching position upstream from and close to the reaction chamber;

wherein the branching flow path communicates with a first gas discharge port closed by a first seal film which is openable by needle insertion for supplying the sample liquid from the liquid introduction port to the branching position;

wherein the reaction chamber communicates with a second gas discharge port closed by a second seal film which is openable by needle insertion for supplying the sample liquid beyond the branching position to the reaction chamber; and wherein the hole-making mechanism comprises a first hole-making needle for perforating the first seal film, and a second hole-making needle for perforating the second seal film.

16. The analytical tool according to claim 14, wherein said at least one flow path extends in a plane that is parallel to the separation film.

17. The analytical tool according to claim 16, further comprising a liquid receiving portion for retaining the sample liquid passed through the separation film, the liquid receiving portion communicating with the liquid introduction port and said at least one flow path, and wherein the separation film is spaced from a bottom surface of the liquid receiving portion.

18. The analytical tool according to claim 17, further comprising:
- a substrate in which the liquid receiving portion and said at least one flow path are formed;
- a cover in which the liquid introduction port, the first discharge port and the second discharge port are formed; and
- an adhesive layer interposed between the substrate and the cover, the adhesive layer including a through-hole for fitting the separation film.

19. The analytical tool according to claim 18, wherein said at least one flow path extends radially from the liquid receiving portion.

20. The analytical tool according to claim 18, wherein a plurality of flow paths are provided for communicating with a plurality of reaction chambers, respectively; and
- wherein the plurality of flow paths communicate with the second discharge port via a common flow path formed in the cover.

* * * * *